United States Patent
Hafer et al.

(10) Patent No.: US 9,586,719 B2
(45) Date of Patent: Mar. 7, 2017

(54) ACTIVATION METHODS FOR VOLATILE DISPENSER

(71) Applicant: The Dial Corporation, Scottsdale, AZ (US)

(72) Inventors: Kevin Hafer, Chandler, AZ (US); James Clark, Chicago, IL (US); Matthew Freeborn, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 135 days.

(21) Appl. No.: 14/644,374

(22) Filed: Mar. 11, 2015

(65) Prior Publication Data

US 2016/0264290 A1 Sep. 15, 2016

(51) Int. Cl.
| | | |
|---|---|---|
| *A61L 9/12* | (2006.01) | |
| *B65D 17/00* | (2006.01) | |
| *A01M 1/20* | (2006.01) | |
| *A61M 11/04* | (2006.01) | |
| *A61M 15/00* | (2006.01) | |
| *A61L 9/00* | (2006.01) | |
| *B65D 51/22* | (2006.01) | |
| *A61M 21/02* | (2006.01) | |

(52) U.S. Cl.
CPC ........... *B65D 17/16* (2013.01); *A01M 1/2044* (2013.01); *A61L 9/00* (2013.01); *A61L 9/127* (2013.01); *A61M 11/04* (2013.01); *A61M 15/0041* (2014.02); *B65D 51/225* (2013.01); *A61M 21/02* (2013.01); *B65D 2101/0023* (2013.01)

(58) Field of Classification Search
CPC .................. B65D 17/16; B65D 51/225; B65D 2101/0023; A01M 1/2044; A61L 9/127; A61L 9/00; A61M 21/02; A61M 2021/0016; A61M 15/0041; A61M 11/04
USPC .................................. 239/6, 44, 47, 49, 51.5
See application file for complete search history.

(56) References Cited

U.S. PATENT DOCUMENTS

| | | | | |
|---|---|---|---|---|
| 7,281,670 | B2 * | 10/2007 | Lakatos | A01M 1/2044 239/49 |
| 8,750,693 | B2 * | 6/2014 | Sharma | A01M 1/2044 239/44 |
| 2006/0175425 | A1 | 8/2006 | McGee et al. | |
| 2010/0314461 | A1 | 12/2010 | Gruenbacher et al. | |
| 2014/0183273 | A1 | 7/2014 | Hafer et al. | |

FOREIGN PATENT DOCUMENTS

| | | |
|---|---|---|
| CN | 2673871 Y | 1/2005 |
| JP | 08-038585 A | 2/1996 |
| JP | 2010-259544 A | 11/2010 |

OTHER PUBLICATIONS

PCT International Search Report (PCT/US2016/020845) dated Jun. 15, 2016.

* cited by examiner

*Primary Examiner* — Steven J Ganey
(74) *Attorney, Agent, or Firm* — P. Scott Smith (57) ABSTRACT

Methods and devices are provided for volatile fluid dispensers with novel activation mechanisms. The device includes a container assembly that includes a reservoir that is sealed to contain a volatile fluid, and an internal barrier. The device also includes a wicking assembly that includes a wick and a puncture element. The application of a force along a longitudinal axis of the wick to the puncture element breaks an internal barrier and allows the fluid in the reservoir to contact the wick.

12 Claims, 6 Drawing Sheets

ACTIVATION METHODS FOR VOLATILE DISPENSER

FIELD OF THE INVENTION

The present invention generally relates to dispensers for volatile material, and more particularly relates to apparatuses and methods for activation of dispensers for volatile liquids.

BACKGROUND OF THE INVENTION

Aqueous and non-aqueous liquid air fresheners have gained popularity for providing a pleasant aroma to an environment. There are a variety of types of dispensers for aqueous and non-aqueous liquid air fresheners. Dispensers may also be used to assist in the evaporation of other volatile liquids. Such other volatile liquids may include aqueous scent mixtures, insect repellants, or odor-based deterrents for animals or humans.

Some dispensers for volatile fluids, such as aqueous and non-aqueous liquid air fresheners, use electricity to drive the evaporation of the volatile fluids. Conversely, other dispensers for volatile fluids do not use electricity, and may provide a large surface area from which the volatile fluid may evaporate.

During handling and storage, some non-electric dispensers may maintain the volatile fluid separate from the large evaporative surface area to prevent premature dispersion of the volatile fluid. During use, these dispensers may require multiple assembly steps to put the volatile fluid in contact with the large evaporative surface area. The multiple assembly steps may be cumbersome for a user and lead to a less than satisfactory user experience. In an alternate approach, the volatile fluid may contact the large evaporative surface area. In this approach, premature evaporation during handling and storage is prevented by using a cap or other cover to seal the assembly from the outside environment. However, this second approach is also not desirable due to aesthetic considerations, complexity, and leakage concerns.

Accordingly, it is desirable to provide a dispenser for volatile fluids that may be easily assembled by a user. In addition, it is desirable for such a dispenser to maintain the volatile fluid separate from the evaporative surface area until a user assembles the unit. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A device is provided for activating a reservoir. The device comprises a container assembly and a wicking assembly. The container assembly comprises a reservoir that is sealed to prevent an escape of a fluid, and an internal barrier. The wicking assembly comprises a wick and a puncture element. The container and wicking assemblies are provided such that the internal barrier of the container assembly is broken by the application of a force on the puncture element along a longitudinal axis of the wick, and the breaking of the internal barrier allows the fluid to contact the wick.

A method is provided for producing a device to activate a reservoir. The method comprises providing a container assembly that comprises a reservoir, placing a fluid into the reservoir, sealing the fluid within the reservoir, and affixing a wicking assembly that comprises a wick and a puncture element to the container assembly. The container assembly and wicking assembly so produced are such that an internal barrier separating the fluid in the reservoir from the wick is broken by application of a force on the puncture element along a longitudinal axis of the wick, and the breaking of the internal barrier allows the fluid in the reservoir to contact the wick.

A consumer product is provided for dispensing a volatile fluid. The consumer product comprises a container assembly, a wicking assembly, and an outer housing assembly. The container assembly comprises a reservoir that is sealed to prevent an escape of a volatile fluid, an internal barrier, and a fitment. The wicking assembly comprises a wick and a puncture element. The outer housing assembly comprises a rib and a slot into which the container assembly and wicking assembly may be asserted. The container assembly and wicking assembly are provided as a single unit, and the insertion of the container assembly and the wicking assembly into the outer housing assembly causes the rib of the outer housing assembly to apply a force to the puncture element along a longitudinal axis of the wick, and the force applied to the puncture element along a longitudinal axis of the wick breaks the internal barrier, allowing the volatile fluid to contact the wick.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

As noted above, volatile fluid dispensers may be a popular way to imbue an environment with a pleasant aroma by facilitating evaporation of the volatile fluid. Volatile fluid dispensers may promote the evaporation of the volatile fluid by either electric or non-electric mechanisms.

Volatile fluids may provide an olfactory sensation. For example, the volatile fluid may include a fragrance, such that dispensing the volatile fluid may cause the environment around the dispenser to become imbued with the scent of the fragrance. In another example, the volatile fluid may include an insect repellent, such that dispensing the volatile fluid may cause insects to avoid the environment around the dispenser. In this example, the volatile fluid dispenser may not produce an olfactory sensation in humans. In yet another example, the volatile fluid may have an unpleasant odor, and the volatile fluid dispenser may thus cause the surrounding environment to have an unpleasant odor, whereby acting as a deterrent for humans or animals. A volatile fluid dispenser that produces an unpleasant odor may be used, for example, to deter house pets from furniture or areas of a house where they may be unwanted or unsafe. A volatile fluid dispenser that is intended to act as a deterrent to non-human creatures (for example, pets or insects) may contain a volatile fluid with an odor that is imperceptible to humans, or that may be perceived as pleasant by humans. In a further example, a volatile fluid may also include aromatherapeutic agents. In a still further example, a volatile fluid may also include mood-enhancing substances. It is also possible for a volatile fluid to contain more than one of the aforementioned properties or additives; for example, a volatile fluid could include an aromatherapeutic agent, a fragrance and an insect repellent. In another example, a volatile fluid could contain both an aromatherapeutic agent and a mood-enhancing substance. The volatile fluid may also contain a carrier fluid, which may be an oil, water, an organic solvent, a silicone, or combinations thereof.

The ease of assembly of a volatile fluid dispenser may be a factor in consumer appeal. For example, aromatic volatile fluids may cause skin irritation and therefore it may be desirable to prevent contact of the volatile fluid with skin. Accordingly, it is desirable to provide a volatile fluid dispenser that is easy to assemble and whose assembly does not risk spilling a volatile fluid contained therein.

The present specification is directed to activation methods and mechanisms for volatile fluid dispensers, and may be used in either electric or non-electric volatile fluid dispensers. The present specification provides a novel mechanism to maintain the volatile fluid separately from the elements that promote the evaporation of the volatile fluid, while also providing facile activation by a user.

Figure 1:
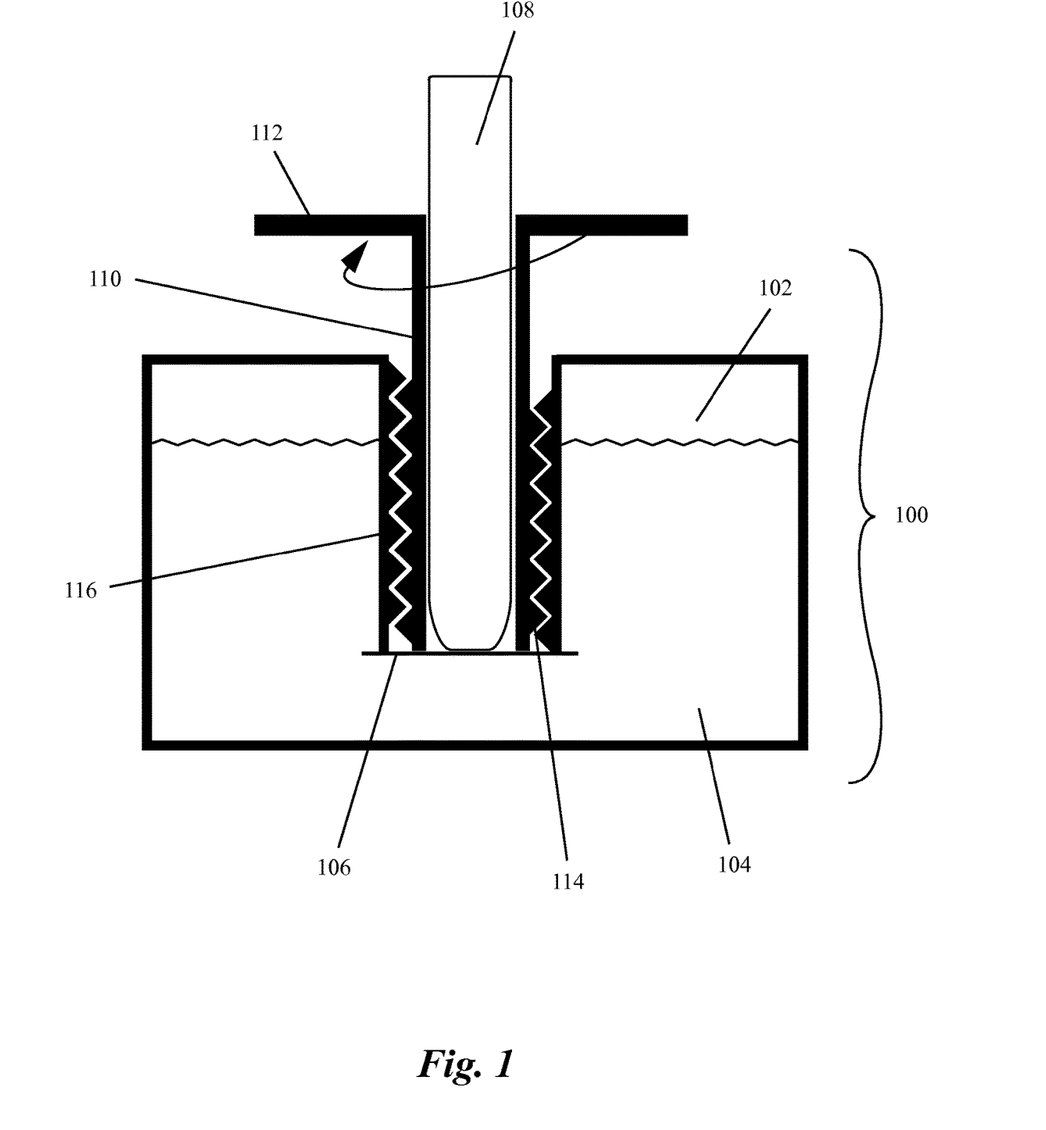
FIG. 1 is a cross-sectional diagram of a container assembly and a wicking assembly prior to activation, according to an example of the principles described herein.

Turning now to the figures, FIG. 1 is a cross-sectional diagram of a container assembly and a wicking assembly (collectively the volatile fluid dispenser (100)) according to an example of the principles described herein, shown prior to activation. The container assembly of FIG. 1 includes a reservoir (102), which contains a volatile fluid (104). The container assembly of FIG. 1 also includes an internal barrier (106), which may be broken upon activation of the volatile fluid dispenser (100). The container assembly of FIG. 1 also includes a fitment (116), which in the example shown in FIG. 1 has threading which may be used to engage a puncture element (110). The wicking assembly of FIG. 1 includes a wick (108), which may contact the volatile fluid (104) in the reservoir (102) once the volatile fluid dispenser (100) is activated. The wicking assembly of FIG. 1 also includes a puncture element (110), which may be used to puncture or break the internal barrier (106). The puncture element (110) may include activation levers (112) to assist in activation of the puncture element (110). The puncture element (110) may also include an engagement structure (114) to engage a fitment (116) on the container assembly. The fitment (116) and the engagement structure (114) used for the puncture element (110) to engage the fitment (116) may have corresponding threading, which may guide the motion of the puncture element (110) along a longitudinal axis of the wick (108) during activation of the volatile fluid dispenser (100). While FIG. 1 specifically depicts a threaded engagement between the puncture element (110) and the fitment (116), other types of engagement may be implemented according to the principles described herein.

The container assembly may be the portion of the dispenser (100) that includes the reservoir (102). The reservoir (102) contains a fluid, which may be a volatile fluid (104). The reservoir (102) may be sealed to prevent the premature escape of a volatile fluid (104). The seal of the reservoir (102) may be a surface that prevents the volatile fluid (104) contained in the reservoir (102) from prematurely escaping.

In addition to a reservoir (102) that is sealed to prevent an escape of a fluid, the container assembly may also include an internal barrier (106). Such an internal barrier (106) may be a surface that separates the wick (108) of the wicking assembly from the volatile fluid (104) contained within the reservoir (102). The internal barrier (106) may prevent premature contact of the volatile fluid (104) contained within the reservoir (102) with the wick (108) of the wicking assembly during handling and storage. The activation of the volatile fluid dispenser (100) may occur by breakage of the internal barrier (106). The breaking of the internal barrier (106) separating the volatile fluid (104) in the reservoir (102) from the wick (108) may occur by any method that destroys the integrity of the internal barrier (106), such that the volatile fluid (104) is allowed to contact the wick (108). For example, the internal barrier (106) may be shattered, ruptured, punctured or otherwise manipulated to break the internal barrier (106) and allow the volatile fluid (104) to access the wick (108).

Figure 2:
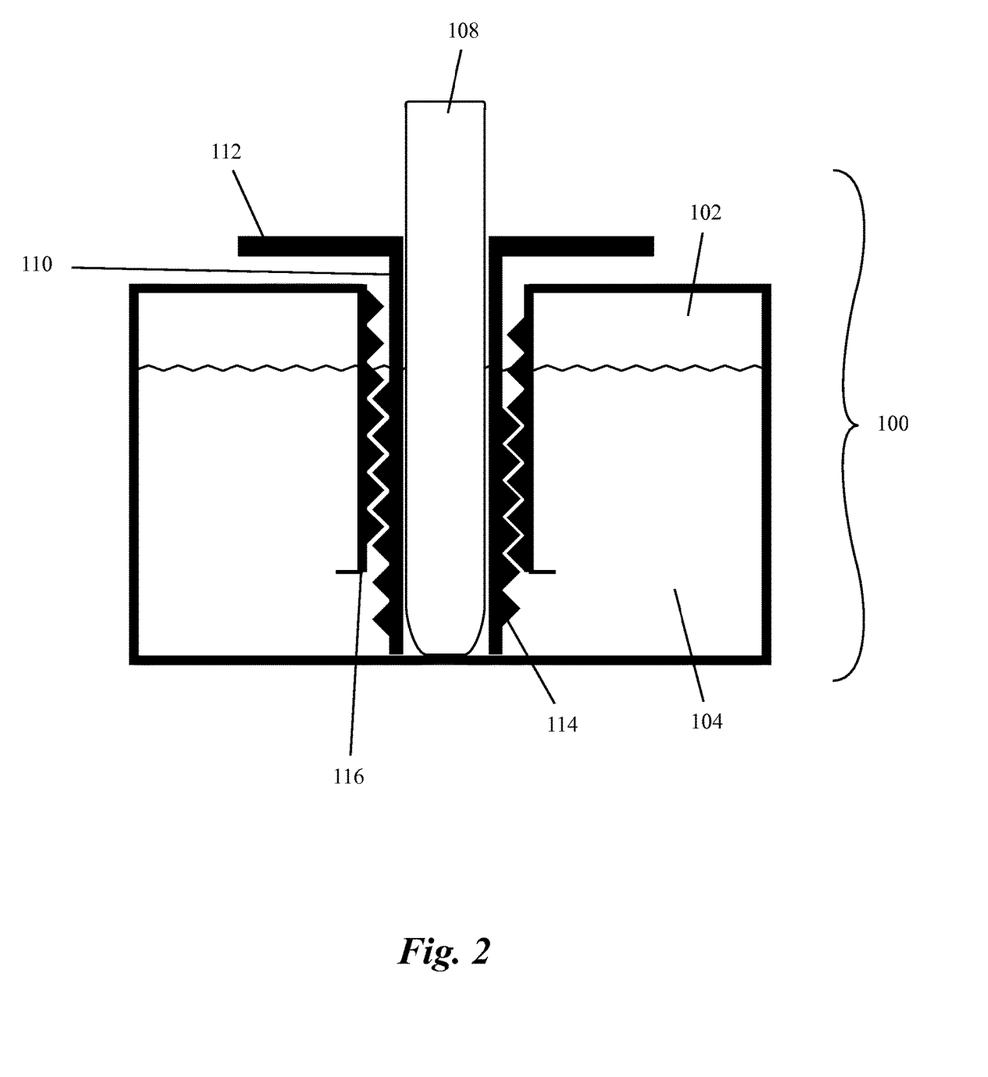
FIG. 2 is a cross-sectional diagram of the container and wicking assemblies of FIG. 1 after activation, according to an example of the principles described herein.

FIG. 2 is a cross-sectional diagram of the container and wicking assemblies (100) of FIG. 1 after activation, according to an example of the principles described herein. In the example of FIG. 2, the puncture element (110) that includes an activation lever (112) has been rotated (along the arrow shown in FIG. 1), causing the puncture element (110) to move downward along a longitudinal axis of the wick (108). For example, a user, may cause the threading on the fitment (116) and engagement structure (114) to engage by rotating the activation lever (112). Such a rotation may cause the puncture element (110) to break the internal barrier (FIG. 1, 106) separating the wick (108) from the volatile fluid (104) contained within the reservoir (102), whereby activating the dispenser (100). In this example, the puncture element (110) has been rotated through an angle of at least 360° (where the precise angle may depend on the slope and type of engagement of the engagement structure (114) used for the puncture element (110)). In the activated state depicted in FIG. 2, the volatile fluid (104) is able to contact the wick (108), which may allow the volatile fluid (104) to move up the wick (108) by capillary action, thus activating the volatile fluid dispenser (100). In one example, the puncture element (110) may have small teeth on its bottom surface to allow the volatile fluid (104) to flow to the wick (108). In another example, there may be a gap between the bottom of the reservoir (102) and the puncture element (110) to allow access of the volatile fluid (104) contained within the reservoir (102) to the wick (108).

The example of FIGS. 1 and 2 is exemplary, and does not represent all types of volatile fluid dispensers (100) that may be used to dispense a volatile fluid (104) according to the principles described herein. For example, the fitment (116) may include an engagement structure that guides the puncture element (110) to move through a smaller or larger angle during activation, or the engagement of the puncture element (110) with the fitment (116) may be accomplished by several tabs on the puncture element (110), and corresponding slots on the fitment (116).

In one example, the seal applied to the reservoir (102) to contain the volatile fluid (104) and the internal barrier (106) that is broken to activate the volatile fluid dispenser (100) are the same surface. In another example, the seal that is applied to the reservoir (102) to contain the volatile fluid (104) and the internal barrier (106) that is broken to activate the volatile fluid dispenser (100) are different surfaces. In other words, the seal of the reservoir (102) and the internal barrier (106) may both be components of a container assembly that includes a reservoir (102), and each may fulfill a different function. Depending on the arrangement of the elements of the volatile fluid dispenser (100), both the seal of the reservoir (102) and the internal barrier (106) may be provided by a single structure, or may be provided by different structures. In the example shown in FIGS. 1 and 2, either arrangement is possible. For example, a seal applied to the reservoir (102) to contain the volatile fluid (104) may be different from the internal barrier (106) if the seal is on an outer surface of the reservoir (102), which may provide more facile manufacturing of such a device. In another example, a seal applied to the reservoir (102) to contain the volatile fluid (104) may be the same surface as the internal barrier (106), which may be assembled by inverting the reservoir (102), filling the inverted reservoir (102) with a volatile fluid (104), and applying the internal barrier (106) as a seal to the reservoir (102) to contain the volatile fluid (104).

In the example of FIGS. 1 and 2, the internal barrier (106) separating the volatile fluid (104) contained within the reservoir (102) from the wick (108) may be either flexible or rigid. A flexible internal barrier (106) may provide for more facile manufacturing; conversely, a rigid internal barrier (106) may provide a more discrete break upon activation. Additionally, a flexible internal barrier (106) may distort its shape such that the opening caused by a puncture element (110) is relatively small, whereas a rigid internal barrier (106) may provide an opening that is larger, for example at least as large as the combined area of the wick (108) and the puncture element (110). A rigid internal barrier (106) may provide a larger opening because it is not readily distorted, and thus the movement of the puncture element (110) through the internal barrier (106) will cause an opening at least as large as the puncture element (110).

In some examples, the reservoir (102) may also include a second barrier that provides a seal to contain the volatile fluid (104) within the reservoir (102). Such a second barrier may prevent leakage of the volatile fluid (104) from the reservoir (102) during storage and transport. Other arrangements of the elements of the volatile fluid dispenser (100) may also allow such a second barrier to be applied in order to prevent leakage of the volatile fluid (104) following activation of the volatile fluid dispenser (100). Thus, in some examples the second barrier may have a direct interface with the volatile fluid (104) contained in the reservoir (102), while in other examples the second barrier only has a direct interface with the volatile fluid (104) contained in the reservoir (102) following activation of the volatile fluid dispenser (100). In still further examples, the second barrier may be omitted.

If a second barrier is included in the volatile fluid dispenser (100), the second barrier may be either flexible or rigid. A flexible barrier may provide for more facile manufacturing, while a rigid barrier may provide a consumer with the perception of greater structural integrity.

The container and wicking assemblies (100) may also include a fitment (116). A fitment (116) may be a component that may guide the motion of the puncture element (110). In the example shown in FIGS. 1-2, the fitment (116) may be part of the container assembly, and may guide the puncture element (110) through a spiral pathway, such that the spiral moves along a longitudinal axis of the wick (108). In another example, the fitment (116) may guide the puncture element (110) to move directly along a longitudinal axis of the wick (108) without rotation. The fitment (116) may serve to engage the puncture element (110), and guide the motion of the puncture element (110) along a longitudinal axis of the wick (108).

As depicted in FIGS. 1-2, a fitment (116) may be formed as part of the container assembly, or may be later added to the container assembly. A fitment (116) may also be added as part of the wicking assembly. For example, the fitment (116) may be combined with an internal barrier (106) prior to joining the fitment (116) with the container assembly. In such an event, the interface between the fitment (116) and the reservoir (102) may provide a seal to the reservoir (102) in order to contain the volatile fluid (104). If the fitment (116) is added to the container and wicking assemblies (100) as a part of the wicking assembly, the fitment (116) may not have a direct interface with the volatile fluid (104) contained within the reservoir (102) prior to activation of the volatile fluid dispenser (100). In such an example, it is also possible that the fitment (116) does not have a direct interface with the volatile fluid (104) at any point during the life of the volatile fluid dispenser (100).

The container assembly may be provided as a single unit with a wicking assembly, such as that shown in FIG. 1. The wicking assembly may include a wick (108), which may draw in the volatile fluid (104) through capillary action to an evaporative surface, which may be an emanator pad. The wick (108) may be made of any material that is suitable for the distribution of a volatile fluid (104) into the surrounding environment. For example, the wick (108) may be a porous material that is either synthetic or naturally produced. In one example, the wick (108) is made of bamboo. In another example, the wick (108) is made from cotton. In yet another example, the wick (108) is synthetically produced, for example from a porous plastic. In another example, the wick (108) may be made from fiber. In a further example, the wick (108) may be made from a ceramic material of either natural or synthetic origin. In a still further example, the wick (108) may be made from wood. In another example, the wick (108) may be made from cellulose. In a further example, the wick (108) may be made from paper. It is also possible for the wick (108) to be made from combinations of suitable materials, either as layers or blends.

The wicking assembly may include a puncture element (110). The puncture element (110) of the wicking assembly may be able to move along a longitudinal axis of the wick (108). In the example shown in FIGS. 1 and 2, the motion of the puncture element (110) along the longitudinal axis of the wick (108) may be through a spiral pathway. In other examples, the motion of the puncture element (110) may be along a longitudinal axis of the wick (108) without rotation about said axis. The puncture element (110) may include a number of activation levers (112), which may be attached to the puncture element (110) in any manner that allows the activation levers (112) to be used to control the motion of the puncture element (110).

The activation levers (112) may be used to control the motion of the puncture element (110). In one example, the activation levers (112) are disposed on either side of the wick (108), and may be used to maneuver the puncture element (110) to move about a longitudinal axis of the wick (108). In another example, a single activation lever (112) is used, and may be disposed on a single side of the wick (108). In a further example, an activation lever (112) may take a different form, for example a disc (which may have a hole through which the wick (108) extends), or teeth.

For the purposes of the present specification, the term "activation lever" may be used broadly to encompass any structure capable of manipulating the motion of the puncture element (110), and may or may not be a lever. Additionally, the activation lever (112) may be engaged by an outer housing assembly, or may be manipulated directly by a user. For example, the activation lever (112) may be provided by a number of tabs that are disposed above the reservoir (102) of the container assembly and are connected to the puncture element (110). In another example, the activation lever (112) may be provided by a number of teeth, which may be placed on a surface of the reservoir (102), and may engage a corresponding set of teeth on an outer housing assembly or another element that may be provided to facilitate the activation of the volatile fluid dispenser (100), for example a hollow cylinder with teeth that correspond to a set of teeth which act as the activation lever (112) of the puncture element (110).

The puncture element (110) may also include an engagement structure (114) that facilitates the engagement of the puncture element (110) with the fitment (116) to guide the motion of the puncture element (110) along a longitudinal axis of the wick (108). Such an engagement structure (114) may take a variety of forms. For example, the engagement structure (114) shown in FIG. 1 may be threading, which interacts with corresponding threading on the fitment (116), such that the rotation of the puncture element (110) moves the puncture element (110) along a longitudinal axis of the wick (108). In another example, the engagement structure (114) may be protrusions along the side of the puncture element (110) that are parallel to a longitudinal axis of the wick (108), such that the puncture element (110) is guided through a motion along a longitudinal axis of the wick (108) without rotation about said axis. The engagement structure (114) may interact with a corresponding component of the fitment (116) in order to guide the motion of the puncture element (110). Alternatively, the engagement structure (114) may interact with a corresponding component of the fitment (116) in order to ensure that the wicking assembly and the container assembly are, and remain, a single unit. For example, the engagement structure (114) may include a number of spines or spikes, which allow the puncture element (110) to rotate freely within the fitment (116), and may interact with ribs on the fitment (116) in order to ensure that any motion of the puncture element (110) along a longitudinal axis of the wick (108) is toward the internal barrier (106) of the container assembly. In another example, the engagement structure (114) may be omitted entirely, such that the puncture element (110) and the fitment (116) engage one another as two concentric cylinders. In such an example, the fitment (116) may guide the motion of the puncture element (110) along a longitudinal axis of the wick (108), and the puncture element (110) may be able to rotate freely within the fitment (116).

The puncture element (110) may be able to move independently of the wick (108), or may move in combination with the wick (108). For example, in the activation of the volatile fluid dispenser (100) shown in FIGS. 1 and 2, the puncture element (110) may rotate about a longitudinal axis of the wick (108), and in doing so, move through a spiral pathway with an overall motion along a longitudinal axis of the wick (108). In one example, the wick (108) may also rotate with the puncture element (110), and the wick (108) and puncture element (110) may move as a single unit. In another example, the wick (108) may move independently of the puncture element (110), and the wick (108) may remain stationary while the puncture element (110) is moved.

In the example of FIGS. 1 and 2, an outer housing assembly may be used in order to engage the activation levers (112) of the puncture element (110) and mediate its rotation about a longitudinal axis of the wick (108), whereby guiding its motion along the longitudinal axis of the wick (108) to break the internal barrier (106) and activate the volatile fluid dispenser (100). However, in another example, the volatile fluid dispenser (100) of FIGS. 1 and 2 may be activated in a similar manner without the use of an outer housing assembly. In such an example, a user may grasp the activation levers (112) on the puncture element (110) and use them to rotate the puncture element (110) to accomplish the same motion that would otherwise be accomplished by engagement with an outer housing assembly.

Figure 3:
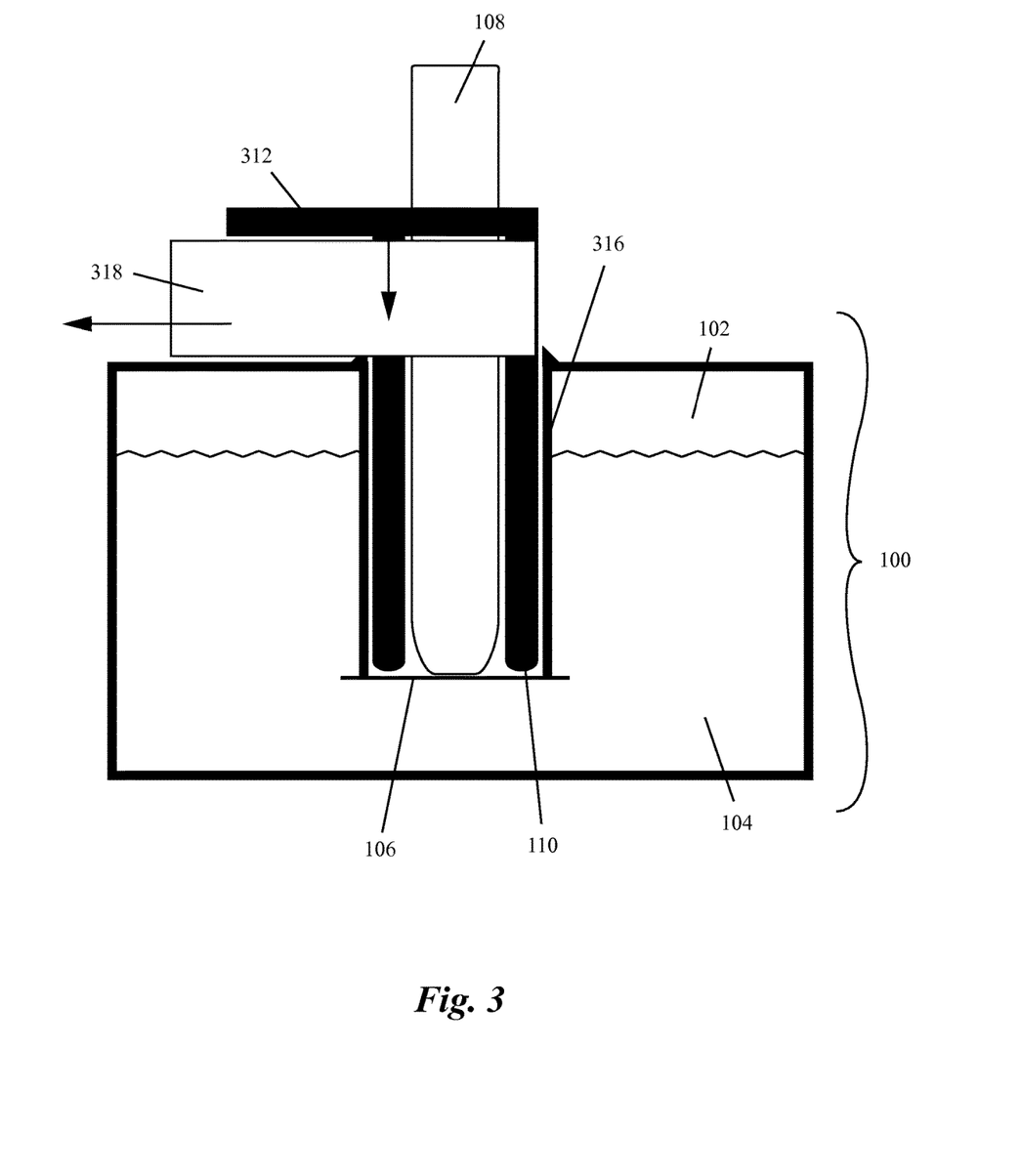
FIG. 3 is a cross-sectional diagram of a container assembly and a wicking assembly prior to activation, according to an example of the principles described herein.

FIG. 3 is a cross-sectional diagram of a container assembly and a wicking assembly (collectively the volatile fluid dispenser (100)) prior to activation, according to an example of the principles described herein. The container assembly of this example includes a reservoir (102) that contains a volatile fluid (104). The container assembly of this example also includes an internal barrier (106). In this example, the internal barrier (106) is attached to a fitment (316), which may also serve to seal the reservoir (102). For example, the internal barrier (106) may be engaged with a fitment (316) that is attached to the reservoir (102) containing a volatile fluid (104) so as to seal the volatile fluid (104) within the reservoir (102). The fitment (316) depicted in the example of FIG. 3 may guide the motion of a puncture element (110) by engaging the puncture element (110) as two concentric cylinders, allowing free rotation of the puncture element (110) within the fitment (316). The wicking assembly of FIG. 3 includes a wick (108), as well as a puncture element (110). In the example shown in FIG. 3, the puncture element (110) includes an activation lever (312). In the example shown in FIG. 3, the activation lever (312) is a single lever, which may be used to apply a compressive force to the puncture element (110) in order to cause the puncture element (110) to break the internal barrier (106) and activate the volatile fluid dispenser (100). The volatile fluid dispenser (100) of FIG. 3 may also be provided with a removable collar (318). A removable collar (318) may be placed between the activation lever (312) and the top of the reservoir (102) in order to prevent the puncture element (110) from prematurely breaking the internal barrier (106).

Volatile fluid dispensers (100) according to the present specification may be provided with a removable collar (318). Such a removable collar (318) may maintain a set distance between an activation lever (312) and a reservoir (102), whereby maintaining a set distance between a puncture element (110) and an internal barrier (106), and preventing the premature activation of the volatile fluid dispenser (100). A removable collar (318) may be made from any suitable material, such as, for example, foam, wood, plastic, metal, etc. The removable collar (318) may be disposed about the puncture element (110), and may prevent the motion of the puncture element (110) in the direction that would activate the dispenser (100). A removable collar (318) may have a recessed surface to receive the activation lever (312), or the activation lever (312) may sit on top of the removable collar (318). In another example, a removable collar (318) may be a solid block with a slot into which the activation lever (312) is inserted.

Figure 4:
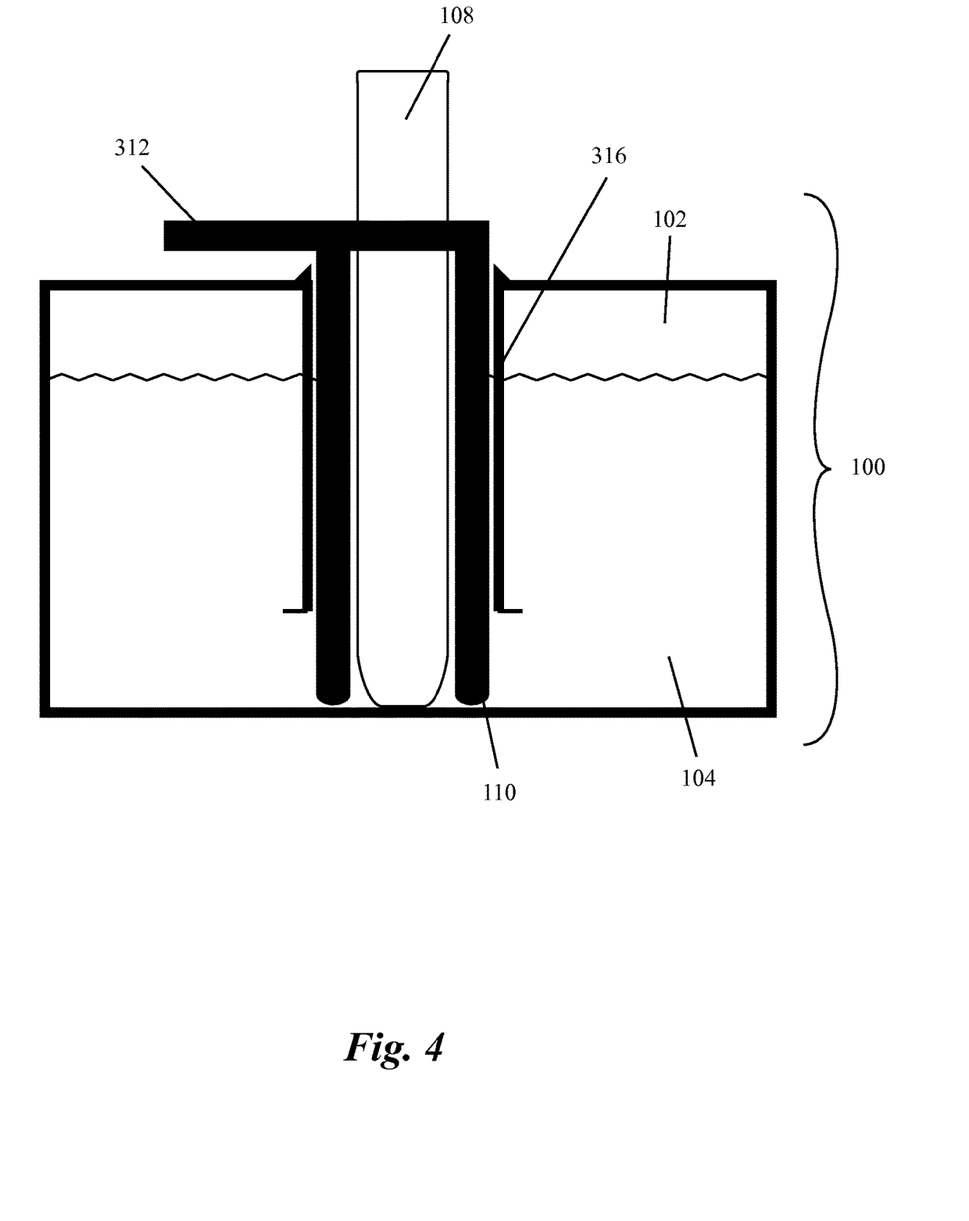
FIG. 4 is a cross-sectional diagram of the container and wicking assemblies of FIG. 3 after activation, according to an example of the principles described herein.

After the removable collar (318) is removed, the container and wicking assemblies (100) of FIG. 3 may be activated. FIG. 4 shows a cross-sectional diagram of the container and wicking assemblies of FIG. 3 after activation. In the activated device, the removable collar (FIG. 3, 318) has been removed, the wick (108) and the puncture element (110) have been moved downward, ruptured the internal barrier (FIG. 3, 106) and activated the dispenser (100) by allowing the volatile fluid (104) contained within the reservoir (102) to contact the wick (108).

The example shown in FIGS. 3-4 is exemplary, and does not represent all types of volatile fluid dispensers (100) that may be used to dispense a volatile fluid (104) according to the principles described herein. For example, while the puncture element (110) is able to rotate freely within the fitment (316) in the example of FIGS. 3-4, in another example, the fitment (316) may have slots that are engaged by corresponding tabs on the puncture element (110). In another example, the wick (108) remains stationary during the activation process, and does not move with the puncture element (110).

Figure 5:
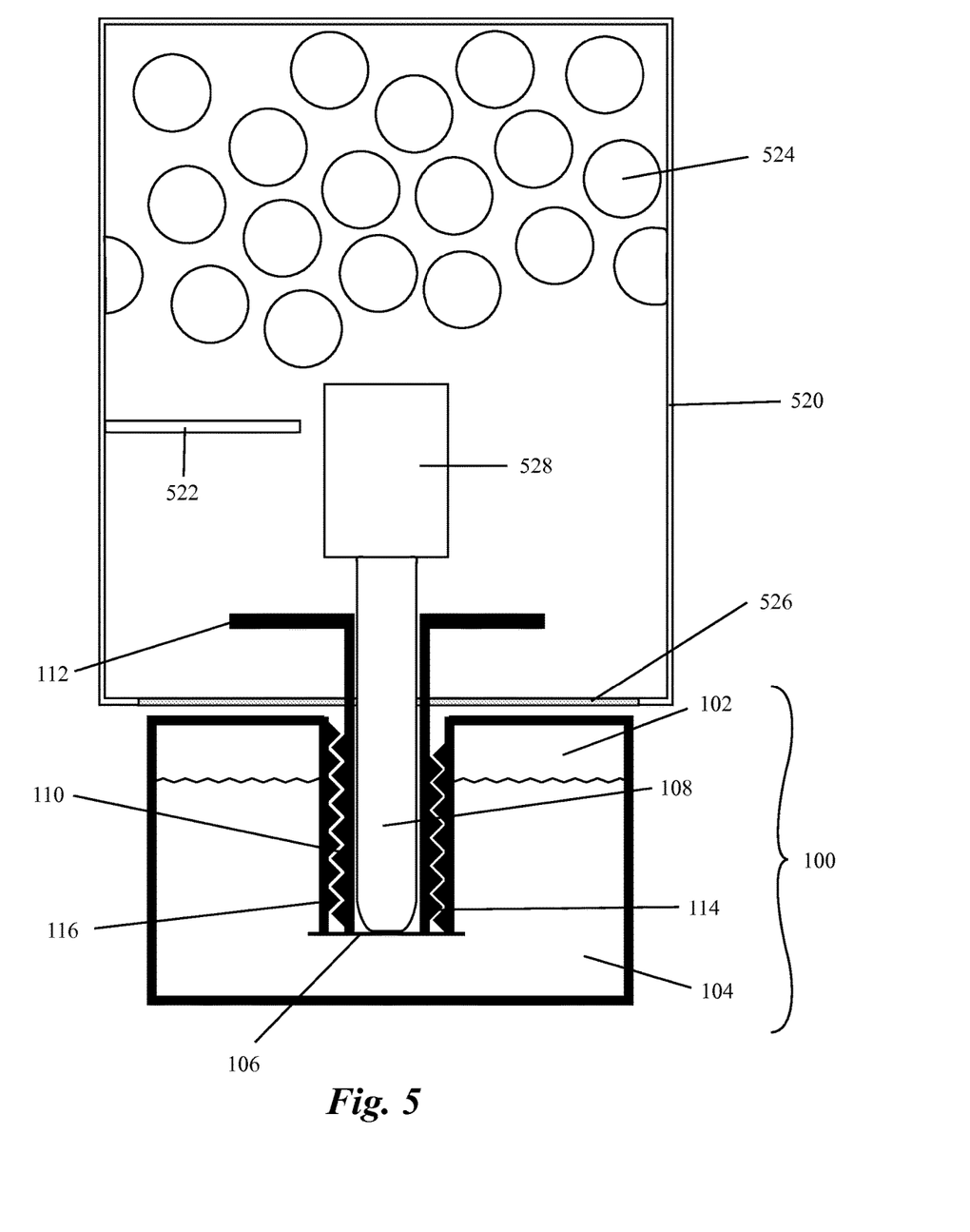
FIG. 5 is a cross-sectional diagram showing the partial insertion of a container assembly and a wicking assembly into an outer housing assembly, according to an example of the principles described herein.

FIG. 5 is a cross-sectional diagram of a container assembly and a wicking assembly (collectively the volatile fluid dispenser (100)), prior to activation, partially inserted into an outer housing assembly (520), according to an example of the principles described herein. The volatile fluid dispenser (100) shown in FIG. 5 may be similar to the volatile fluid dispenser (100) shown in FIG. 1. The volatile fluid dispenser (100) may include a container assembly and a wicking assembly. The container assembly may include a reservoir (102) that is filled with a volatile fluid (104). The container assembly may include a fitment (116) and an internal barrier (106). The wicking assembly may include a wick (108) and a puncture element (110). The puncture element (110) may be equipped with activation levers (112) and an engagement structure (114) to engage the fitment (116) of the container assembly. The outer housing assembly (520) shown in FIG. 5 may be equipped with a rib (522) that engages the activation levers (112) of the puncture element (110). The outer housing assembly (520) may be equipped with a slot (526) into which the volatile fluid dispenser (100) may be inserted. The outer housing assembly (520) may be equipped with ventilation openings (524) to allow the volatile fluid (104) to evaporate into the surrounding environment. The example of FIG. 5 may show an emanator pad (528), which may be part of the wicking assembly, container assembly or outer housing assembly (520).

The volatile fluid dispenser (100) may also be provided with an outer housing assembly (520). Such an outer housing assembly (520) may engage the activation lever (112) of the puncture element (110). In one example, the engagement of the activation lever (112) may occur by a rib (522) that couples the rotation of the puncture element (110) to the outer housing assembly (520). In another example, the engagement of the activation lever (112) with an outer housing assembly (520) may occur by a set of teeth on the outer housing assembly (520) which pair with corresponding teeth on the activation lever (112), and similarly cause the rotation of the puncture element (110) within the container and wicking assemblies to be coupled to the outer housing assembly (520). In yet another example, the outer housing assembly (520) may engage the activation lever (112) by preventing the activation lever (112) from being fully inserted into the outer housing assembly (520), such that the engagement of the container and wicking assemblies with the outer housing assembly (520) causes a compressive force to be exerted on the activation lever (112), whereby exerting a compressive force on the puncture element (110). Such a compressive force may cause the puncture element (110) to move along a longitudinal axis of the wick (108), whereby breaking an internal barrier (106) separating the volatile fluid (104) contained in the reservoir (102) from the wick (108).

If an outer housing assembly (520) is used in conjunction with the volatile fluid dispenser (100), such an outer housing assembly (520) may provide some portion of the external surface of the assembled volatile fluid dispenser (100). In one example, the outer housing assembly (520) provides an external surface around the reservoir (102) and the wick (108) of the container and wicking assemblies, which external surface may have ventilation openings (524) to allow the evaporation of the volatile fluid (104) into the surrounding environment once the dispenser (100) is activated. In another example, the outer housing assembly (520) provides an external surface around the wick (108) and/or emanator pad (528), but encloses only a portion of the reservoir (102) containing the volatile fluid (104). In yet another example, the outer housing assembly (520) is provided already attached to the container and wicking assemblies (100), and the outer housing assembly (520) includes a tab on an external surface of the container and wicking assemblies (100) that allows a user to directly move the puncture element (110) in order to activate the volatile fluid dispenser (100). In this example, the outer housing assembly (520) may not enclose either the reservoir (102) or the wick (108) and/or emanator pad (528) of the container and wicking assemblies (100).

An emanator pad (528) may be an element with increased surface area to promote the evaporation of the volatile fluid (104) from its surface. In one example, the wick (108) is connected to, and considered to be a single unit with, the emanator pad (528). In another example, the wick (108) may engage an emanator pad (528) that may be part of the container assembly or an outer housing assembly (520). In yet another example, the wick (108) also provides the emanator pad (528); a portion of the wick (108) that directly contacts the volatile fluid (104) may be considered the wick (108), while a portion of the wick (108) which promotes evaporation of the volatile fluid (104) may be considered the emanator pad (528).

The wick (108) and emanator pad (528) may be composed of the same material, or may be composed of different materials. The emanator pad (528) may be made of any material that is suitable for the distribution of a volatile fluid (104) into the surrounding environment. For example, the emanator pad (528) may be a porous material that is either synthetic or naturally produced. In one example, the emanator pad (528) is made of bamboo. In another example, the emanator pad (528) is made from cotton. In yet another example, the emanator pad (528) is synthetically produced, for example from a porous plastic. In further examples, the emanator pad (528) may be made from fiber, a ceramic material of either natural or synthetic origin, wood, cellulose, paper, or combinations thereof. The wick (108) may draw a volatile fluid (104) to the emanator pad (528) by capillary action; the wick (108) and the emanator pad (528) may be made from the same material, or may be made from different materials. For example, the wick (108) may be made from bamboo, while the emanator pad (528) may be made from cotton. In another example, the wick (108) may be made from a porous plastic, while the emanator pad (528)

may be made from bamboo. In a further example, both the wick (108) and emanator pad (528) may be made from cotton. In another example, the wick (108) may be made from layered fiber and wood, while the emanator pad (528) may be made from blended paper and cellulose.

If the volatile fluid dispenser (100) uses electrical resistance to increase the rate of evaporation of the volatile fluid (104), the wick (108) and/or emanator pad (528) may also include an electrically resistive material, such as a ceramic or metallic material, which may be either porous or non-porous. In another example, the volatile fluid dispenser (100) promotes an enhanced evaporation of the volatile fluid (104) by promoting faster exchange of air surrounding the emanator pad (528) (which may be accomplished by an electrical device, without any electrical contact with either the wick (108) or the emanator pad (528)).

Conversely, if the volatile fluid dispenser (100) does not use electricity, the rate of evaporation of the volatile fluid (104) into the surrounding environment may be controlled by the accessible surface area of the wick (108) and emanator pad (528), for example. In another example, the volatile fluid dispenser (100) does not use electricity and the rate of evaporation of the volatile fluid (104) into the surrounding environment is controlled by the size and number of ventilation openings (524) in the outer housing assembly (520), thus making the rate of exchange of air around the wick (108) and/or emanator pad (528) the controlling factor in the rate of evaporation of the volatile fluid (104).

Figure 6:
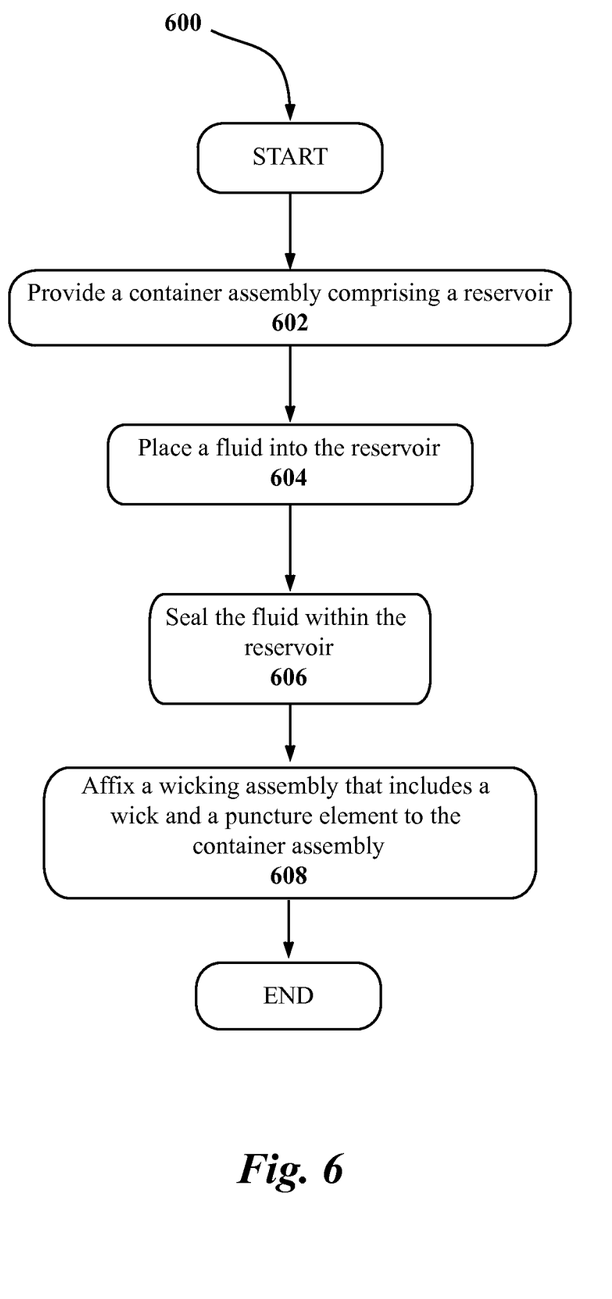
FIG. 6 is a flowchart of a method of making a volatile fluid dispenser, according to an example of the principles described herein.

The present specification also includes a method to produce a device according to the present specification. FIG. 6 is a flowchart of a method (600) of making a volatile fluid dispenser according to an example of the principles described herein. Such a device may include a container assembly and a wicking assembly, and may also include an outer housing assembly (FIG. 5, 520).

The method (600) includes providing (block 602) a container assembly that includes a reservoir (FIG. 1, 102), placing (block 604) a fluid into that reservoir (FIG. 1, 102), which may be part of a container assembly. The method (600) also includes sealing (block 606) the fluid within the reservoir (FIG. 1, 102). The method (600) further includes affixing (block 608) a wicking assembly that includes a wick (FIG. 1, 108) and a puncture element (FIG. 1, 110) to the container assembly. An internal barrier (FIG. 1, 106) separating the fluid in the reservoir (FIG. 1, 102) from the wick (FIG. 1, 108) may be broken by application of a force on the puncture element (FIG. 1, 110) along a longitudinal axis of a wick (FIG. 1, 108), and the breaking of the internal barrier (FIG. 1, 106) may allow the fluid in the reservoir (FIG. 1, 102) to contact the wick (FIG. 1, 108).

Additionally, the method (600) may also include additional operations. Such additional operations may include affixing a second seal, or attaching a removable collar (FIG. 3, 318) to prevent premature activation of the device, which may be a volatile fluid dispenser (FIG. 1, 100).

The operations of the method (600) may be performed in any order. For example, the wicking assembly may be affixed to the container assembly prior to filling the reservoir (FIG. 1, 102) with a fluid. Conversely, a fluid may be added to a reservoir (FIG. 1, 102) prior to affixing the wicking assembly. Additionally, the seal that is applied (block 606) to seal the fluid within the reservoir (FIG. 1, 102) may or may not include the internal barrier (FIG. 1, 106) that is broken to activate the dispenser, although it is possible that these are the same surface, or that the seal that is applied (block 606) includes, but is not the same as, the internal barrier (FIG. 1, 106). For example, the seal that is applied (block 606) may be the internal barrier itself (FIG. 1, 106), may be a pre-assembly that includes both a fitment (FIG. 3, 116) and an internal barrier (FIG. 3, 106), or may be a separate seal on the reservoir (FIG. 1, 102).

The present specification also provides for a consumer product for dispensing a volatile fluid (FIG. 5, 104) according to an example of the principles described herein. A consumer product for dispensing a volatile fluid (FIG. 5, 104) may include a container assembly, a wicking assembly, and an outer housing assembly (FIG. 5, 520). The container assembly may include a reservoir (FIG. 5, 102) that is sealed to prevent an escape of a volatile fluid (FIG. 5, 104), an internal barrier (FIG. 5, 106), and a fitment (FIG. 5, 116). The wicking assembly may include a wick (FIG. 5, 108) and a puncture element (FIG. 5, 110). The outer housing assembly (FIG. 5, 520) may include a rib (FIG. 5, 522) and a slot (FIG. 5, 526) into which the container assembly and the wicking assembly may be inserted. The container assembly, wicking assembly and outer housing assembly (FIG. 5, 520) may be provided such that the container assembly and the wicking assembly are provided as a single unit. The insertion of the container assembly and the wicking assembly into the outer housing assembly (FIG. 5, 520) may cause the rib (FIG. 5, 522) of the outer housing assembly (FIG. 5, 520) to interact with the activation levers (FIG. 5, 112) of the puncture element (FIG. 5, 110), and this interaction may apply a force to the puncture element (FIG. 5, 110) along a longitudinal axis of the wick (FIG. 5, 108). The application of a force to the puncture element (FIG. 5, 110) along a longitudinal axis of the wick (FIG. 5, 108) may break the internal barrier (FIG. 5, 106) of the container assembly, which may allow contact of the volatile fluid (FIG. 5, 104) in the reservoir (FIG. 5, 102) with the wick (FIG. 5, 108) of the wicking assembly.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A consumer product for dispensing a volatile fluid, comprising:
   a container assembly comprising:
      a reservoir that is sealed to prevent an escape of a volatile fluid;
      an internal barrier; and
      a fitment;
   a wicking assembly comprising:
      a wick; and
      a puncture element; and
   an outer housing assembly comprising:
      a rib; and
      a slot into which the container assembly and wicking assembly may be inserted;
   in which:
      the container assembly and the wicking assembly are provided as a single unit;

the insertion of the container assembly and the wicking assembly into the outer housing assembly causes the rib to apply a force to the puncture element along a longitudinal axis of the wick; and the force applied to the puncture element along a longitudinal axis of the wick breaks the internal barrier, allowing contact of the volatile fluid with the wick.

2. The consumer product of claim 1, further comprising a removable collar to prevent premature activation of the consumer product.

3. The consumer product of claim 1, in which the fitment guides the motion of the puncture element through a spiral path.

4. The consumer product of claim 1, in which the fluid in the reservoir comprises a volatile fragrance, an aromatherapeutic agent, an insecticide, a repellant, or insecticide.

5. The consumer product of claim 1, in which the internal barrier is flexible.

6. The consumer product of claim 1, in which the internal barrier is rigid.

7. The consumer product of claim 1, in which the wick is a porous solid.

8. The consumer product of claim 1, in which the fitment guides the motion of the puncture element through a spiral path.

9. The consumer product of claim 1, in which the fitment guides the motion of the puncture element to break the internal barrier such that the puncture element does not rotate.

10. The consumer product of claim 1, in which the puncture element comprises an activation lever.

11. The consumer product of claim 1, in which the wicking assembly further comprises an emanator pad disposed on the wick.

12. The consumer product of claim 1, further comprising a removable collar to prevent premature activation of the reservoir.

* * * * *